US009849023B2

(12) United States Patent
Hall et al.

(10) Patent No.: US 9,849,023 B2
(45) Date of Patent: Dec. 26, 2017

(54) REDUCED-PRESSURE SYSTEMS, DEVICES, AND METHODS FOR TREATING A TISSUE SITE THAT INCLUDES A FISTULA

(71) Applicant: KCI LICENSING, INC., San Antonio, TX (US)

(72) Inventors: Colin John Hall, Poole (GB); Richard Paul Mormino, San Antonio, TX (US)

(73) Assignee: KCI Licensing, Inc., San Antonio, TX (US)

( * ) Notice: Subject to any disclaimer, the term of this patent is extended or adjusted under 35 U.S.C. 154(b) by 253 days.

(21) Appl. No.: 14/268,720

(22) Filed: May 2, 2014

(65) Prior Publication Data
US 2014/0309601 A1 Oct. 16, 2014

Related U.S. Application Data

(62) Division of application No. 13/253,841, filed on Oct. 5, 2011, now Pat. No. 8,758,314.

(Continued)

(51) Int. Cl.
*A61F 5/445* (2006.01)
*A61M 27/00* (2006.01)
*A61M 1/00* (2006.01)

(52) U.S. Cl.
CPC .......... *A61F 5/445* (2013.01); *A61M 1/0088* (2013.01); *A61F 2005/4455* (2013.01); *A61M 27/00* (2013.01)

(58) Field of Classification Search
CPC .. A61F 5/445; A61F 2005/4455; A61F 5/448; A61M 1/0088; A61M 1/0023; A61M 27/00

(Continued)

(56) References Cited

U.S. PATENT DOCUMENTS 1,355,846 A 10/1920 Rannells
2,547,758 A 4/1951 Keeling
(Continued)

FOREIGN PATENT DOCUMENTS

AU 550575 A1 3/1986
AU 745271 4/1999
(Continued)

OTHER PUBLICATIONS

N. A. Bagautdinov, "Variant of External Vacuum Aspiration in the Treatment of Purulent Diseases of the Soft Tissues," Current Problems in Modern Clinical Surgery: Interdepartmental Collection, edited by V. Ye Volkov et al. (Chuvashia State University, Cheboksary, U.S.S.R. 1986);pp. 94-96 (copy and certified translation).

(Continued)

*Primary Examiner* — Lynne Anderson (57) ABSTRACT

Systems, methods, and devices are disclosed that involve a fistula-isolating device for use when reduced pressure is applied to a wound bed having a fistula. In one instance, the fistula-isolating device includes an adjustable passageway member and a perimeter member that contracts under reduced pressure and that automatically accommodates wound beds of different heights. In another instance, the fistula-isolating device involves a body shaped as a frustro-conical body that is readily sized for different depth wound beds. Other systems, methods, and devices are presented.

14 Claims, 8 Drawing Sheets

Related U.S. Application Data (60) Provisional application No. 61/394,999, filed on Oct. 20, 2010.

(58) Field of Classification Search
USPC ........ 604/319, 313, 289, 337, 541, 317, 290
See application file for complete search history.

(56) References Cited

U.S. PATENT DOCUMENTS

| | | | |
|---|---|---|---|
| 2,632,443 A | | 3/1953 | Lesher |
| 2,682,873 A | | 7/1954 | Evans et al. |
| 2,910,763 A | | 11/1959 | Lauterbach |
| 2,969,057 A | | 1/1961 | Simmons |
| 3,066,672 A | | 12/1962 | Crosby, Jr. et al. |
| 3,216,420 A | * | 11/1965 | Smith et al. ............... 604/328 |
| 3,367,332 A | | 2/1968 | Groves |
| 3,520,300 A | | 7/1970 | Flower, Jr. |
| 3,568,675 A | | 3/1971 | Harvey |
| 3,648,692 A | | 3/1972 | Wheeler |
| 3,682,180 A | | 8/1972 | McFarlane |
| 3,826,254 A | | 7/1974 | Mellor |
| 4,080,970 A | | 3/1978 | Miller |
| 4,096,853 A | | 6/1978 | Weigand |
| 4,139,004 A | | 2/1979 | Gonzalez, Jr. |
| 4,165,748 A | | 8/1979 | Johnson |
| 4,184,510 A | | 1/1980 | Murry et al. |
| 4,233,969 A | | 11/1980 | Lock et al. |
| 4,245,630 A | | 1/1981 | Lloyd et al. |
| 4,256,109 A | | 3/1981 | Nichols |
| 4,261,363 A | | 4/1981 | Russo |
| 4,275,721 A | | 6/1981 | Olson |
| 4,284,079 A | | 8/1981 | Adair |
| 4,297,995 A | | 11/1981 | Golub |
| 4,333,468 A | | 6/1982 | Geist |
| 4,373,519 A | | 2/1983 | Errede et al. |
| 4,382,441 A | | 5/1983 | Svedman |
| 4,392,853 A | | 7/1983 | Muto |
| 4,392,858 A | | 7/1983 | George et al. |
| 4,419,097 A | | 12/1983 | Rowland |
| 4,465,485 A | | 8/1984 | Kashmer et al. |
| 4,475,909 A | | 10/1984 | Eisenberg |
| 4,480,638 A | | 11/1984 | Schmid |
| 4,525,166 A | | 6/1985 | Leclerc |
| 4,525,374 A | | 6/1985 | Vaillancourt |
| 4,540,412 A | | 9/1985 | Van Overloop |
| 4,543,100 A | | 9/1985 | Brodsky |
| 4,548,202 A | | 10/1985 | Duncan |
| 4,551,139 A | | 11/1985 | Plaas et al. |
| 4,569,348 A | | 2/1986 | Hasslinger |
| 4,605,399 A | | 8/1986 | Weston et al. |
| 4,608,041 A | | 8/1986 | Nielsen |
| 4,640,688 A | | 2/1987 | Hauser |
| 4,655,754 A | | 4/1987 | Richmond et al. |
| 4,664,662 A | | 5/1987 | Webster |
| 4,710,165 A | | 12/1987 | McNeil et al. |
| 4,733,659 A | | 3/1988 | Edenbaum et al. |
| 4,743,232 A | | 5/1988 | Kruger |
| 4,758,220 A | | 7/1988 | Sundblom et al. |
| 4,787,888 A | | 11/1988 | Fox |
| 4,826,494 A | | 5/1989 | Richmond et al. |
| 4,838,883 A | | 6/1989 | Matsuura |
| 4,840,187 A | | 6/1989 | Brazier |
| 4,863,449 A | | 9/1989 | Therriault et al. |
| 4,872,450 A | | 10/1989 | Austad |
| 4,878,901 A | | 11/1989 | Sachse |
| 4,897,081 A | | 1/1990 | Poirier et al. |
| 4,906,233 A | | 3/1990 | Moriuchi et al. |
| 4,906,240 A | | 3/1990 | Reed et al. |
| 4,919,654 A | | 4/1990 | Kalt et al. |
| 4,941,882 A | | 7/1990 | Ward et al. |
| 4,953,565 A | | 9/1990 | Tachibana et al. |
| 4,969,880 A | | 11/1990 | Zamierowski |
| 4,985,019 A | | 1/1991 | Michelson |
| 5,037,397 A | | 8/1991 | Kalt et al. |
| 5,086,170 A | | 2/1992 | Luheshi et al. |
| 5,092,858 A | | 3/1992 | Benson et al. |
| 5,100,396 A | | 3/1992 | Zamierowski |
| 5,134,994 A | | 8/1992 | Say |
| 5,149,331 A | | 9/1992 | Ferdman et al. |
| 5,167,613 A | | 12/1992 | Karami et al. |
| 5,176,663 A | | 1/1993 | Svedman et al. |
| 5,215,522 A | | 6/1993 | Page et al. |
| 5,232,453 A | | 8/1993 | Plass et al. |
| 5,261,893 A | | 11/1993 | Zamierowski |
| 5,278,100 A | | 1/1994 | Doan et al. |
| 5,279,550 A | | 1/1994 | Habib et al. |
| 5,298,015 A | | 3/1994 | Komatsuzaki et al. |
| 5,342,376 A | | 8/1994 | Ruff |
| 5,344,415 A | | 9/1994 | DeBusk et al. |
| 5,358,494 A | | 10/1994 | Svedman |
| 5,437,622 A | | 8/1995 | Carion |
| 5,437,651 A | | 8/1995 | Todd et al. |
| 5,527,293 A | | 6/1996 | Zamierowski |
| 5,549,584 A | | 8/1996 | Gross |
| 5,556,375 A | | 9/1996 | Ewall |
| 5,607,388 A | | 3/1997 | Ewall |
| 5,636,643 A | | 6/1997 | Argenta et al. |
| 5,645,081 A | | 7/1997 | Argenta et al. |
| 6,071,267 A | | 6/2000 | Zamierowski |
| 6,135,116 A | | 10/2000 | Vogel et al. |
| 6,241,747 B1 | | 6/2001 | Ruff |
| 6,287,316 B1 | | 9/2001 | Agarwal et al. |
| 6,345,623 B1 | | 2/2002 | Heaton et al. |
| 6,488,643 B1 | | 12/2002 | Tumey et al. |
| 6,493,568 B1 | | 12/2002 | Bell et al. |
| 6,553,998 B2 | | 4/2003 | Heaton et al. |
| 6,814,079 B2 | | 11/2004 | Heaton et al. |
| 7,708,724 B2 | | 5/2010 | Weston |
| 7,722,586 B2 | * | 5/2010 | Mullejans ............... A61F 5/441 |
| | | | 604/332 |
| 8,273,017 B1 | * | 9/2012 | Moreno ................... A61B 1/32 |
| | | | 600/203 |
| 8,771,243 B2 | | 7/2014 | Khan et al. |
| 9,078,990 B1 | | 7/2015 | Obst et al. |
| 2002/0077661 A1 | | 6/2002 | Saadat |
| 2002/0115951 A1 | | 8/2002 | Norstrem et al. |
| 2002/0120185 A1 | | 8/2002 | Johnson |
| 2002/0143286 A1 | | 10/2002 | Tumey |
| 2003/0060786 A1 | * | 3/2003 | Olsen ...................... A61F 5/448 |
| | | | 604/342 |
| 2006/0079852 A1 | | 4/2006 | Bubb et al. |
| 2008/0161778 A1 | | 7/2008 | Steward |
| 2008/0287892 A1 | * | 11/2008 | Khan et al. ............... 604/313 |
| 2009/0131893 A1 | * | 5/2009 | Priest et al. ............... 604/342 |
| 2011/0106032 A1 | * | 5/2011 | Kratky .................... A61F 5/448 |
| | | | 604/337 |
| 2012/0046690 A1 | * | 2/2012 | Blom ................. A61B 17/0057 |
| | | | 606/213 |

FOREIGN PATENT DOCUMENTS

| | | |
|---|---|---|
| AU | 755496 | 2/2002 |
| CA | 2005436 | 6/1990 |
| DE | 26 40 413 A1 | 3/1978 |
| DE | 43 06 478 A1 | 9/1994 |
| DE | 295 04 378 U1 | 10/1995 |
| EP | 0100148 A1 | 2/1984 |
| EP | 0117632 A2 | 9/1984 |
| EP | 0161865 A2 | 11/1985 |
| EP | 0358302 A2 | 3/1990 |
| EP | 1018967 B1 | 8/2004 |
| GB | 692578 | 6/1953 |
| GB | 2 195 255 A | 4/1988 |
| GB | 2 197 789 A | 6/1988 |
| GB | 2 220 357 A | 1/1990 |
| GB | 2 235 877 A | 3/1991 |
| GB | 2 329 127 B | 3/1999 |
| GB | 2 333 965 A | 8/1999 |
| JP | 4129536 | 4/1992 |
| SG | 71559 | 3/1999 |
| WO | 80/02182 A1 | 10/1980 |
| WO | 87/04626 A1 | 8/1987 |
| WO | 90/10424 A1 | 9/1990 |

(56) References Cited

FOREIGN PATENT DOCUMENTS

| WO | 93/09727 A1 | 5/1993 |
| --- | --- | --- |
| WO | 94/20041 A1 | 9/1994 |
| WO | 96/05873 A1 | 2/1996 |
| WO | 97/18007 A1 | 5/1997 |
| WO | 99/13793 A1 | 3/1999 |

OTHER PUBLICATIONS

Louis C. Argenta, MD and Michael J. Morykwas, PhD; "Vacuum-Assisted Closure: A New Method for Wound Control and Treatment: Animal Studies & Basic Foundation"; Annals of Plastic Surgery, vol. 38, No. 6, Jun. 1997; pp. 553-562.

Susan Mendez-Eastmen, RN; "When Wounds Won't Heal" RN Jan. 1998, vol. 61 (1); Medical Economics Company, Inc., Montvale, NJ, USA; pp. 20-24.

James H. Blackburn, II, MD, et al; "Negative-Pressure Dressings as a Bolster for Skin Grafts"; Annals of Plastic Surgery, vol. 40, No. 5, May 1998, pp. 453-457.

John Masters; "Reliable, Inexpensive and Simple Suction Dressings"; Letters to the Editor, British Journal of Plastic Surgery, 1998, vol. 51 (3), p. 267; Elsevier Science/The British Association of Plastic Surgeons, UK.

S.E. Greer, et al "The Use of Subatmospheric Pressure Dressing Therapy to Close Lymphocutaneous Fistulas of the Groin" British Journal of Plastic Surgery (2000), vol. 53, pp. 484-487.

George V. Letsou, MD., et al; "Stimulation of Adenylate Cyclase Activity in Cultured Endothelial Cells Subjected to Cyclic Stretch"; Journal of Cardiovascular Surgery, vol. 31, 1990, pp. 634-639.

Orringer, Jay, et al; "Management of Wounds in Patients with Complex Enterocutaneous Fistulas"; Surgery, Gynecology & Obstetrics, Jul. 1987, vol. 165, pp. 79-80.

International Search Report for PCT International Application PCT/GB95/01983; dated Nov. 23, 1995.

PCT International Search Report for PCT International Application PCT/GB98/02713; dated Jan. 8, 1999.

PCT Written Opinion; PCT International Application PCT/GB98/02713; dated Jun. 8, 1999.

PCT International Examination and Search Report, PCT International Application PCT/GB96/02802; dated Jan. 15, 1998 & Apr. 29, 1997.

PCT Written Opinion, PCT International Application PCT/GB96/02802; dated Sep. 3, 1997.

Dattilo, Philip P., Jr., et al; "Medical Textiles: Application of an Absorbable Barbed Bi-directional Surgical Suture"; Journal of Textile and Apparel, Technology and Management, vol. 2, Issue 2, Spring 2002, pp. 1-5.

Kostyuchenok, B.M., et al; "Vacuum Treatment in the Surgical Management of Purulent Wounds"; Vestnik Khirurgi, Sep. 1986, pp. 18-21 and 6 page English translation thereof.

Davydov, Yu. A., et al; "Vacuum Therapy in the Treatment of Purulent Lactation Mastitis"; Vestnik Khirurgi, May 14, 1986, pp. 66-70, and 9 page English translation thereof.

Yusupov. Yu. N., et al; "Active Wound Drainage", Vestnik Khirurgi, vol. 138, Issue 4, 1987, and 7 page English translation thereof.

Davydov, Yu. A., et al; "Bacteriological and Cytological Assessment of Vacuum Therapy for Purulent Wounds"; Vestnik Khirurgi, Oct. 1988, pp. 48-52, and 8 page English translation thereof.

Davydov, Yu. A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.

Chariker, Mark E., M.D., et al; "Effective Management of incisional and cutaneous fistulae with closed suction wound drainage"; Contemporary Surgery, vol. 34, Jun. 1989, pp. 59-63.

Egnell Minor, Instruction Book, First Edition, 300 7502, Feb. 1975, pp. 24.

Egnell Minor: Addition to the Users Manual Concerning Overflow Protection—Concerns all Egnell Pumps, Feb. 3, 1983, p. 1.

Svedman, P.: "Irrigation Treatment of Leg Ulcers", The Lancet, Sep. 3, 1983, pp. 532-534.

Chinn, Steven D. et al.: "Closed Wound Suction Drainage", The Journal of Foot Surgery, vol. 24, No. 1, 1985, pp. 76-81.

Arnljots, Björn et al.: "Irrigation Treatment in Split-Thickness Skin Grafting of Intractable Leg Ulcers", Scand J. Plast Reconstr. Surg., vol. 19, 1985, pp. 211-213.

Svedman, P.: "A Dressing Allowing Continuous Treatment of a Biosurface", IRCS Medical Science: Biomedical Technology, Clinical Medicine, Surgery and Transplantation, vol. 7, 1979, p. 221.

Svedman, P. et al.: "A Dressing System Providing Fluid Supply and Suction Drainage Used for Continuous or Intermittent Irrigation", Annals of Plastic Surgery, vol. 17, No. 2, Aug. 1986, pp. 125-133.

K.F. Jeter, T.E. Tintle, and M. Chariker, "Managing Draining Wounds and Fistulae: New and Established Methods," Chronic Wound Care, edited by D. Krasner (Health Management Publications, Inc., King of Prussia, PA 1990), pp. 240-246.

G. Živadinovic, V. Ðukić, Ž. Maksimović, Ð. Radak, and P. Peška, "Vacuum Therapy in the Treatment of Peripheral Blood Vessels," Timok Medical Journal 11 (1986), pp. 161-164 (copy and certified translation).

F.E. Johnson, "An Improved Technique for Skin Graft Placement Using a Suction Drain," Surgery, Gynecology, and Obstetrics 159 (1984), pp. 584-585.

A.A. Safronov, Dissertation Abstract, Vacuum Therapy of Trophic Ulcers of the Lower Leg with Simultaneous Autoplasty of the Skin (Central Scientific Research Institute of Traumatology and Orthopedics, Moscow, U.S.S.R. 1967) (copy and certified translation).

M. Schein, R. Saadia, J.R. Jamieson, and G.A.G. Decker, "The 'Sandwich Technique' in the Management of the Open Abdomen," British Journal of Surgery 73 (1986), pp. 369-370.

D.E. Tribble, "An Improved Sump Drain-Irrigation Device of Simple Construction," Archives of Surgery 105 (1972) pp. 511-513.

C.E. Tennant, "The Use of Hypermia in the Postoperative Treatment of Lesions of the Extremities and Thorax," Journal of the American Medical Association 64 (1915), pp. 1548-1549.

Selections from W. Meyer and V. Schmieden, Bier's Hyperemic Treatment in Surgery, Medicine, and the Specialties: A Manual of Its Practical Application, (W.B. Saunders Co., Philadelphia, PA 1909), pp. 17-25, 44-64, 90-96, 167-170, and 210-211.

V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").

V.A. Kuznetsov & N.A. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").

V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").

V.A.C. ® Therapy Clinical Guidelines: A Reference Source for Clinicians (Jul. 2007).

AU Examination Report No. 1 corresponding to AU2016216545, dated Jul. 28, 2017.

\* cited by examiner

REDUCED-PRESSURE SYSTEMS, DEVICES, AND METHODS FOR TREATING A TISSUE SITE THAT INCLUDES A FISTULA

RELATED APPLICATIONS

This application is a division of U.S. application Ser. No. 13/253,841, entitled "Reduced-Pressure Systems, Devices, And Methods For Treating A Tissue Site That Includes A Fistula," filed 5 Oct. 2011, which claims the benefit, under 35 USC §119(e), of the filing of U.S. Provisional Patent Application Ser. No. 61/394,999, entitled "Reduced-Pressure Systems, Devices, And Methods For Treating A Tissue Site That Includes A Fistula," filed 20 Oct. 2010, both of which are incorporated herein by reference for all purposes.

FIELD

The present disclosure relates generally to medical treatment systems and, more particularly, but not by way of limitation, to systems, devices, and methods for treating with reduced pressure a tissue site that involves a fistula.

BACKGROUND

Clinical studies and practice have shown that providing reduced pressure in proximity to a tissue site augments and accelerates the growth of new tissue at the tissue site. The applications of this phenomenon are numerous, but application of reduced pressure has been particularly successful in treating wounds. This treatment (frequently referred to in the medical community as "negative pressure wound therapy," "reduced pressure therapy," or "vacuum therapy") provides a number of benefits, which may include faster healing and increased formulation of granulation tissue. Typically, when applied to open wounds, reduced pressure is applied to the tissue through a porous pad or other manifold device. The porous pad contains cells or pores that are capable of distributing reduced pressure to the tissue and channeling fluids that are drawn from the tissue. When applied subcutaneously, often the reduced pressure is delivered through a manifold that includes channels and openings in a reduced-pressure delivery apparatus.

A fistula at the tissue site can be problematic with respect to applying reduced pressure to the tissue site. In general terms, a "fistula" is an abnormal passage that leads from an abscess or hollow organ or part to the body surface or from one hollow organ or part to another and that may be surgically created to permit passage of fluids or secretions. As used herein, "fistula" includes, without limitation, enteric fistulas, enterocutaneous fistulas, and stomas. If a fistula were located at a tissue site that is a wound bed that is being treated and if reduced pressure were applied to the whole tissue site, including the fistula, effluent from the fistula would be drawn onto other portions of the tissue site. This would potentially cause slower healing or various issues. The situation may be more challenging with an intestinal fistula because effluent from an intestinal fistula can be corrosive to the wound bed.

SUMMARY

According to illustrative embodiments herein, systems, methods, and devices involve a fistula-isolating device for use when reduced pressure is applied to a wound bed having a fistula. In one illustrative embodiment, the fistula-isolating device includes an adjustable passageway member and a perimeter member that contracts under reduced pressure and that automatically accommodates wound beds of different heights. In another illustrative embodiment, the fistula-isolating device involves a body shaped as a frustro-conical body that is readily sized for different depth wound beds.

According to an illustrative embodiment, a system for providing reduced pressure treatment to a wound bed having a fistula includes a fistula-isolating device for isolating the fistula in the wound bed, a distribution manifold having a fistula aperture for receiving the fistula-isolating device, a sealing member for covering the fistula-isolating device and the distribution manifold to create a sealed space over at least a portion of the wound bed, a reduced-pressure source for supplying a reduced pressure, a reduced-pressure interface fluidly coupled to the distribution manifold, a reduced-pressure delivery conduit fluidly coupled to the reduced-pressure source and to the reduced-pressure interface, and an ostomy appliance fluidly coupled to a first aperture on the first flange member of the fistula-isolating device. The fistula-isolating device includes the first flange member having a first aperture, a second flange member having a second aperture, and an adjustable passageway member coupled to the first flange member and to the second flange member. The adjustable passageway member has a passageway substantially aligned with the first aperture of the first flange member and the second aperture of the second flange member. The adjustable passageway member is variably moveable between a retracted position in which the adjustable passageway member has a length $L_R$ and an extended position in which the adjustable passageway member has a length $L_E$ and wherein $L_E > 3L_R$. The adjustable passageway member is substantially fluid impermeable. The fistula-isolating device includes a perimeter member positioned substantially around an exterior perimeter of the adjustable passageway member and between the first flange member and the second flange member. The perimeter member is configured to contract under reduced pressure.

According to another illustrative embodiment, a fistula-isolating device for isolating a fistula in a wound bed undergoing reduced-pressure treatment includes a first flange member having a first aperture, a second flange member having a second aperture, an adjustable passageway member coupled to the first flange member and to the second flange member. The adjustable passageway member has a passageway substantially aligned with the first aperture of the first flange member and the second aperture of the second flange member. The adjustable passageway member is variably moveable between a retracted position in which the adjustable passageway member has a length $L_R$ and an extended position in which the adjustable passageway member has a length $L_E$ and wherein $L_E > 3L_R$. The adjustable passageway member is substantially fluid impermeable. The fistula-isolating device also includes a perimeter member positioned substantially around an exterior perimeter of the adjustable passageway member and between the first flange member and the second flange member. The perimeter member is configured to contract under reduced pressure.

According to another illustrative embodiment, a method of providing reduced pressure treatment to a wound bed that has a fistula includes providing a fistula-isolating device for isolating the fistula in the wound bed undergoing reduced-pressure treatment and disposing a distribution manifold, which has a fistula aperture for receiving the fistula-isolating device, proximate to the wound bed with the fistula aperture substantially over the fistula. The method further includes covering the fistula-isolating device and the distribution manifold with a sealing member to create a sealed space over at least a portion of the wound bed, providing a reduced-pressure source for supplying a reduced pressure, fluidly coupling the reduced-pressure source to the distribution manifold, and fluidly coupling an ostomy appliance to the first aperture on a first flange member. The fistula-isolating device includes the first flange member having a first aperture, a second flange member having a second aperture, and an adjustable passageway member coupled to the first flange member and to the second flange member. The adjustable passageway member has a passageway substantially aligned with the first aperture of the first flange member and the second aperture of the second flange member. The adjustable passageway member is variably moveable between a retracted position in which the adjustable passageway member has a length $L_R$ and an extended position in which the adjustable passageway member has a length $L_E$ and wherein $L_E > 3L_R$. The adjustable passageway member is substantially fluid impermeable. A perimeter member is positioned substantially around an exterior perimeter of the adjustable passageway member between the first flange member and the second flange member. The perimeter member is configured to contract under reduced pressure.

According to another illustrative embodiment, a system for providing reduced pressure treatment to a wound bed that has a fistula includes a fistula-isolating device for isolating the fistula in the wound bed, a distribution manifold having a fistula aperture for receiving the fistula-isolating device, a sealing member for covering the fistula-isolating device and the distribution manifold to create a sealed space over at least a portion of the wound bed, a reduced-pressure source for supplying a reduced pressure to the sealed space, and an ostomy appliance fluidly coupled to the fistula-isolating device. The fistula-isolating device includes a body that is substantially frusto-conical in shape and has a passageway. The fistula-isolating device also includes a first end and a second end. At least a portion of the body defining the passageway is fluid impermeable.

According to another illustrative embodiment, a system for providing reduced pressure treatment to a wound bed that has a fistula includes a fistula-isolating device for isolating the fistula in the wound bed undergoing reduced-pressure treatment. The fistula-isolating device includes an adjustable passageway member. The adjustable passageway member is configured to move between a retracted position and an extended position and is substantially fluid impermeable. The fistula-isolating device also includes a perimeter member positioned substantially around an exterior perimeter of the adjustable passageway member. The perimeter member is configured to contract under reduced pressure. The system also includes a distribution manifold having a fistula aperture for receiving the fistula-isolating device, a sealing member for covering the fistula-isolating device and the distribution manifold to create a sealed space over at least a portion of the wound bed, a reduced-pressure source for supplying a reduced pressure to the sealed space, and an ostomy appliance fluidly coupled to the adjustable passageway member.

According to an illustrative embodiment, a system for providing reduced pressure to a wound bed that contains a fistula includes a distributor for distributing reduced pressure in the wound bed, an isolation device for isolating the fistula from other portions of the wound bed, a cover for providing a fluid seal over the distributor and the isolation device, a reduced-pressure source fluidly coupled to the distributor, and a collection vessel fluidly coupled to the passageway of the isolation device for receiving fluids from the fistula. The isolation device includes a compressible, fluid-impermeable member, which has a first end, a second end, and a passageway, and a resilient member adjacent to the compressible, fluid-impermeable member that is sized and configured to bias the first end of the compressible, fluid-impermeable member away from the second end of the compressible, fluid-impermeable member.

According to an illustrative embodiment, an ostomy-appliance interface for fluidly coupling an ostomy appliance and a fistula isolating device includes an attachment ring having a body and an aperture. The attachment ring has a first side and a second, patient-facing side. The ostomy-appliance interface further includes a first ostomy-attachment device coupled to the first side of the attachment ring for coupling to the ostomy appliance, a second ostomy-attachment device coupled to the second, patient-facing side for coupling to the fistula isolating device, a first release liner releasably coupled to the first ostomy-attachment device, and a second release liner releasably coupled to the second ostomy-attachment device.

Other aspects, features, and advantages of the illustrative embodiments will become apparent with reference to the drawings and detailed description that follow.

DETAILED DESCRIPTION OF ILLUSTRATIVE EMBODIMENTS

In the following detailed description of the illustrative, non-limiting embodiments, reference is made to the accompanying drawings that form a part hereof. These embodiments are described in sufficient detail to enable those skilled in the art to practice the invention, and it is understood that other embodiments may be utilized and that logical structural, mechanical, electrical, and chemical changes may be made without departing from the spirit or scope of the invention. To avoid detail not necessary to enable those skilled in the art to practice the embodiments described herein, the description may omit certain information known to those skilled in the art. The following detailed description is, therefore, not to be taken in a limiting sense, and the scope of the illustrative embodiments are defined only by the appended claims.

Figure 1:
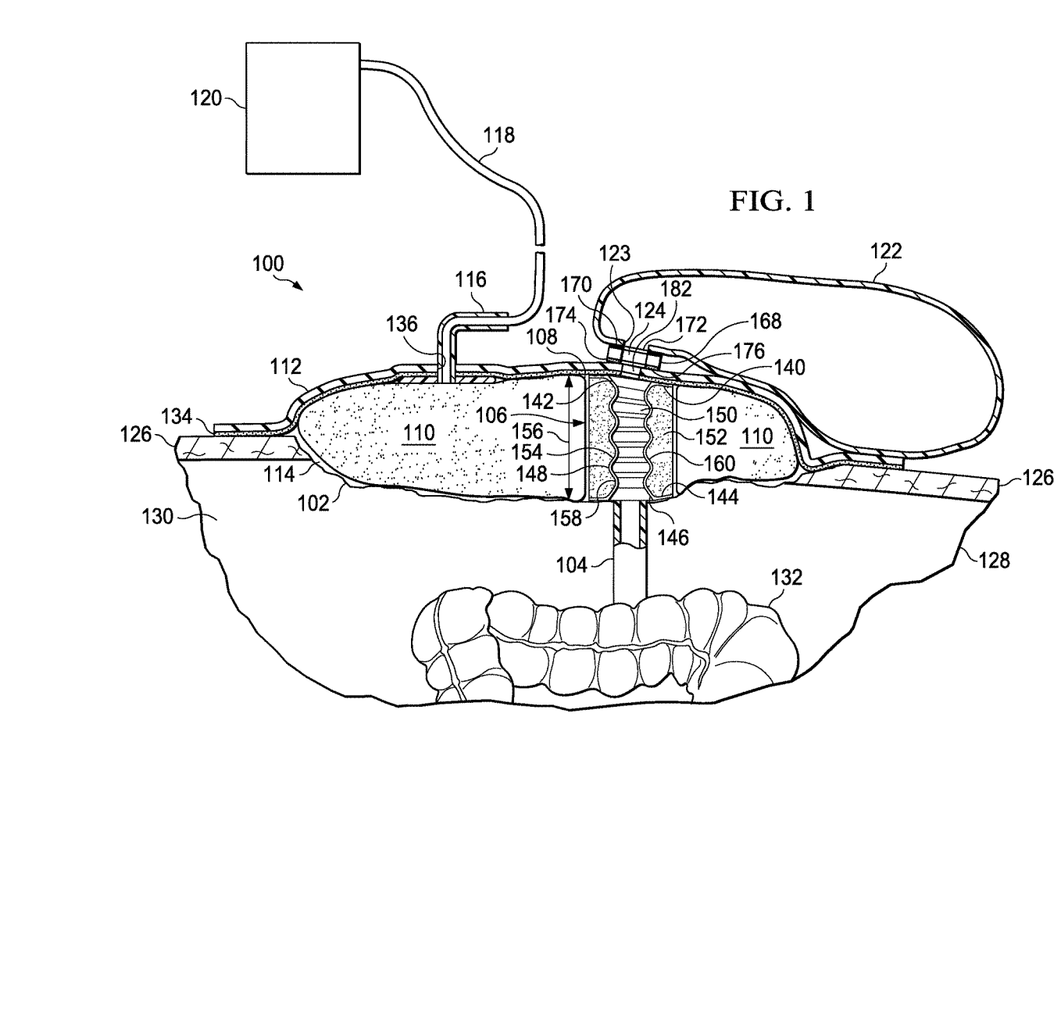
FIG. 1 is a schematic diagram, with a portion shown in cross section, of an illustrative embodiment of a system for providing reduced pressure treatment to a wound bed that includes a fistula.

Referring now to FIGS. 1-6 and initially to FIG. 1, a system 100 for providing reduced pressure treatment to a wound bed 102 that includes a fistula 104 is presented. The fistula 104 may be, for example, an enterocutaneous fistula. By way of introduction, the system 100 includes a fistula-isolating device 106 for isolating the fistula 104 in the wound bed 102 undergoing reduced-pressure treatment. The fistula-isolating device 106 fits within a fistula aperture 108 formed in a distribution manifold 110, which is used to provide reduced pressure therapy to the wound bed 102. A sealing member 112 covers the distribution manifold 110 and the fistula-isolating device 106, and a portion of the patient's epidermis 126 to from a sealed space 114 over the wound bed 102. A reduced-pressure interface 116 provides fluid communication through the sealing member 112 to the sealed space 114. A reduced-pressure delivery conduit 118 fluidly couples the reduced-pressure interface 116 to a reduced-pressure source 120. An ostomy appliance 122 or other collection vessel may be coupled to an ostomy-appliance interface 124, or more generally a collection vessel interface, which is fluidly coupled to the fistula-isolating device 106. In one illustrative embodiment (not explicitly shown), the first flange member 140 may comprise the ostomy-appliance interface 124.

The wound bed 102 may be through epidermis 126 of the patient 128 and involve subcutaneous tissue 130. The system 100 may used on many different types of tissue sites, e.g., bodily tissue of any human, animal, or other organism, including bone tissue, adipose tissue, muscle tissue, dermal tissue, vascular tissue, or any other tissue. Treatment of the wound bed 102 may include removal of fluids, e.g., exudate. In the particular illustrative embodiment shown, the fistula 104 is shown fluidly coupling a portion of the patient's 128 bowel 132 to a portion of the wound bed 102. As used herein, "fistula" includes a stoma.

The distribution manifold 110 is sized by the healthcare provider to fit in the wound bed 102, and the fistula aperture 108 is sized to accommodate the fistula-isolating device 106. The term "manifold" or "distribution manifold" as used herein generally refers to a substance or structure that is provided to assist in applying reduced pressure to, delivering fluids to, or removing fluids from a tissue site, such as the wound bed 102. Unless otherwise indicated, as used throughout this document, "or" does not require mutual exclusivity. The distribution manifold 110 typically includes a plurality of flow channels or pathways that distribute fluids provided to and removed from the tissue site, e.g., the wound bed 102, around the distribution manifold 110. In one illustrative embodiment, the flow channels or pathways are interconnected to improve distribution of fluids provided or removed from the wound bed 102.

The distribution manifold 110 may be a biocompatible material that is capable of being placed in contact with the wound bed 102 and distributing reduced pressure to the wound bed 102. Examples of distribution manifolds may include one or more of the following without limitation: devices that have structural elements arranged to form flow channels, such as, for example, cellular foam, open-cell foam, porous tissue collections, liquids, gels, and foams that include, or cure to include, flow channels; a porous material; foam; gauze; felted mat; a porous foam, which includes a plurality of interconnected cells or pores that act as flow channels; a polyurethane, open-cell, reticulated foam such as GranuFoam® material from Kinetic Concepts, Incorporated of San Antonio, Tex. In some situations, the distribution manifold 110 may also be used to distribute fluids such as medications, antibacterials, growth factors, and various solutions to the wound bed 102. Other layers may be included in or on the distribution manifold 110, such as absorptive materials, wicking materials, hydrophobic materials, and hydrophilic materials.

In one illustrative embodiment, the distribution manifold 110 or portion thereof may be constructed from bioresorbable materials that do not have to be removed from a patient's body following use of the system 100. Suitable bioresorbable materials may include, without limitation, a polymeric blend of polylactic acid (PLA) and polyglycolic acid (PGA). The polymeric blend may also include, without limitation, polycarbonates, polyfumarates, and capralactones. The distribution manifold 110 may further serve in some embodiments as a scaffold for new cell-growth, or a scaffold material may be used in conjunction with the distribution manifold 110 to promote cell-growth. A scaffold is a substance or structure used to enhance or promote the growth of cells or formation of tissue, such as a three-dimensional porous structure that provides a template for cell growth. Illustrative examples of scaffold materials include calcium phosphate, collagen, PLA/PGA, coral hydroxy apatites, carbonates, or processed allograft materials.

The sealing member 112 covers the distribution manifold 110, fistula-isolating device 106, and a portion of intact epidermis 126. The sealing member 112 provides a fluid seal to form the sealed space 114. The fluid seal is a seal adequate to maintain reduced pressure at a desired site given the particular reduced-pressure source 120 or subsystem involved. The sealed space 114 creates a space where reduced pressure may be brought to bear upon the wound bed 102, except the portion isolated by the fistula-isolating device 106. The sealing member 112 may be any material that provides a fluid seal. The sealing member 112 may be formed from one or more of the following: impermeable; semi-permeable materials; elastomeric materials (e.g., natural rubbers, polyisoprene, styrene butadiene rubber, chloroprene rubber, polybutadiene, nitrile rubber, butyl rubber, ethylene propylene rubber, ethylene propylene diene monomer, chlorosulfonated polyethylene, polysulfide rubber, polyurethane (PU), EVA film, co-polyester, or silicones); a silicone drape; 3M Tegaderm® drape; and polyurethane (PU) drape such as one available from Avery Dennison Corporation of Pasadena, Calif.

An attachment device 134 may be used to hold the sealing member 112 against the patient's epidermis 126 or another layer, such as a gasket or additional sealing member. The attachment device 134 may take numerous forms. For example, the attachment device 134 may be a medically acceptable, pressure-sensitive adhesive that extends about a periphery, or a portion of, or all of the sealing member 112. The attachment device 134 may also serve to engage the fistula-isolating device 106.

The reduced-pressure interface 116 may be placed on an aperture 136 formed in the sealing member 112 to provide fluid communication to the sealed space 114. In one illustrative embodiment, the reduced-pressure interface 116 is a T.R.A.C.® Pad or Sensa T.R.A.C.® Pad available from KCI of San Antonio, Tex. The reduced-pressure interface 116 may take any form that provides fluid access to the sealed space 114.

The reduced pressure developed by the reduced-pressure source 120 is delivered through the reduced-pressure delivery conduit 118 to the reduced-pressure interface 116. The reduced-pressure delivery conduit 118 may be any medical conduit, single or multi-lumen, for placing the reduced-pressure interface 116 in fluid communication with the reduced-pressure source 120.

The reduced-pressure source 120 may be any device for supplying a reduced pressure, such as a vacuum pump, wall suction, integrated micro-pump, or other source. While the amount and nature of reduced pressure applied to a tissue site, e.g., wound bed 102, will typically vary according to the application, the reduced pressure will typically be between −5 mm Hg (−667 Pa) and −500 mm Hg (−66.7 kPa), more typically between −75 mm Hg (−9.9 kPa) and −300 mm Hg (−39.9 kPa), and more typically still between −75 mm Hg (−9.9 kPa) and −200 mm Hg (−26.6 kPa). For example, and not by way of limitation, the pressure may be −12, −12.5, −13, −14, −14.5, −15, −15.5, −16, −16.5, −17, −17.5, −18, −18.5, −19, −19.5, −20, −20.5, −21, −21.5, −22, −22.5, −23, −23.5, −24, −24.5, −25, −25.5, −26, −26.5 kPa or another pressure. One illustrative embodiment uses a therapeutic pressure range that is between −75 mm to −175 mm Hg.

Reduced pressure is a pressure less than the ambient pressure at a tissue site that is being subjected to treatment. In most cases, this reduced pressure will be less than the atmospheric pressure at which the patient is located. Alternatively, the reduced pressure may be less than a hydrostatic pressure at the tissue site, e.g., wound bed 102. Unless otherwise indicated, values of pressure stated herein are gauge pressures. The reduced pressure delivered may be constant or varied (patterned or random) and may be delivered continuously or intermittently. Although the terms "vacuum" and "negative pressure" may be used to describe the pressure applied to the tissue site, the actual pressure applied to the tissue site may be more than the pressure normally associated with a complete vacuum. Consistent with the use herein, an increase in reduced pressure or vacuum pressure typically refers to a relative reduction in absolute pressure.

The fistula-isolating device 106 functionally isolates the fistula 104 from other portions of the wound bed 102 so that reduced pressure does not attract effluent from the fistula 104 into the distribution manifold 110. The fistula-isolating device 106 also functions to contract with the distribution manifold 110 and to accommodate different depths of wound beds 102. As suggested by FIGS. 2-3, 6, 7-9, 10, and 11, numerous embodiments of the fistula-isolating device 106 may used as part of the system 100.

Referring now primarily to FIG. 1-3B, a couple of illustrative embodiments of the fistula-isolating device 106 are presented. The fistula-isolating device 106 may include a first flange member 140 having a first flange aperture 142, a second flange member 144 having a second flange aperture 146, and an adjustable passageway member 148 therebetween. The adjustable passageway member 148 is coupled to the first flange member 140 and to the second flange member 144 and has a passageway 150 that is substantially aligned with the first flange aperture 142 and the second flange aperture 146. The adjustable passageway member 148 is fluid impermeable, which means that the adjustable passageway member 148 substantially restricts or prevents the flow of fluids (liquids or gases).

Figure 3A:
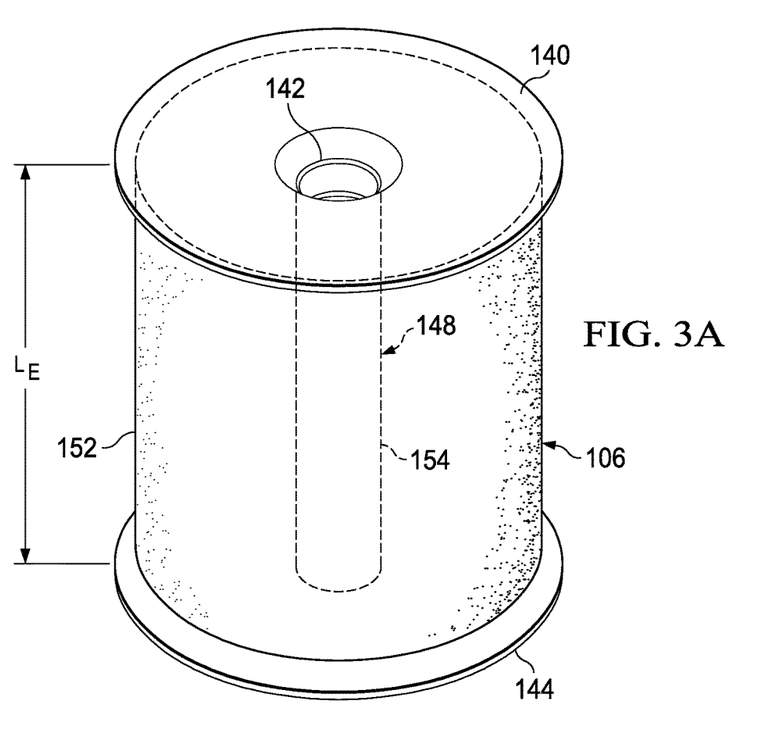
FIG. 3A is a schematic, perspective view of an illustrative embodiment of a fistula-isolating device shown in an extended position.
Figure 3B:
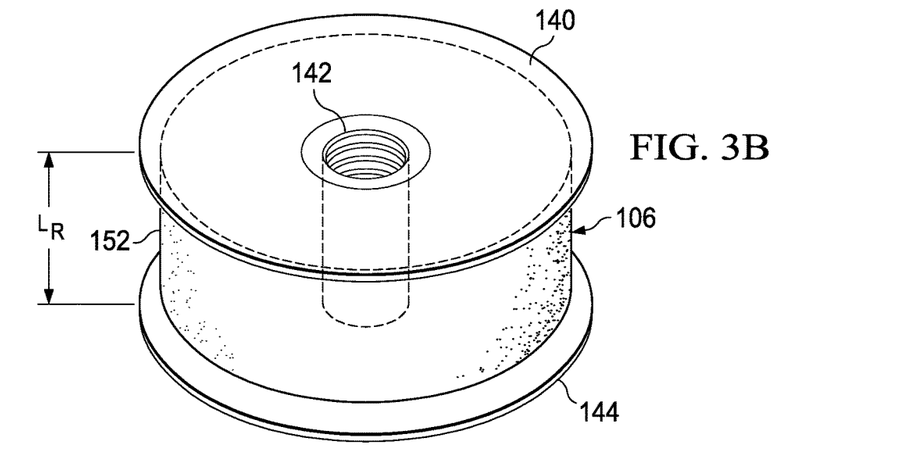
FIG. 3B is a schematic, perspective view of the fistula-isolating device of FIG. 3A shown in the retracted position.

The fistula-isolating device 106 and, accordingly, the adjustable passageway member 148 are variably moveable between an extended position and a retracted position. For example, the fistula-isolating device 106 is shown in FIG. 3A in an extended position and is shown in FIG. 3B in a retracted position. In the retracted position, the adjustable passageway member 148 has a length $L_R$ and in the extended position the adjustable passageway member 148 has a length $L_E$. In an illustrative embodiment the length of the adjustable passageway member 148 in the extended position $L_E$ is at least three times that of the length in the retracted position $L_R$, i.e., $L_E > 3L_R$. In other embodiments the relationships may be different, e.g., $L_E > 2L_R$, $L_E > 4L_R$, $L_E > 5L_R$, $L_E > 6L_R$, $L_E > 8L_R$, $L_E > 10L_R$, or $L_E > 12L_R$. The fistula-isolating device 106 may have various dimensions, and in one illustrative embodiment has a retracted length ($L_R$) in the retracted position of approximately one centimeter (1 cm) or less and may have an extended length ($L_E$) in the extended position of approximately ten centimeters (10 cm) or more.

The fistula-isolating device 106 includes a perimeter member 152 positioned substantially around an exterior perimeter 154 of the adjustable passageway member 148 and between the first flange member 140 and the second flange member 144. In some embodiments, the perimeter member 152 may be coupled to the first flange member 140 and to the second flange member 144 using any known technique, including, without limitation, welding (e.g., ultrasonic or RF welding), bonding, adhesives, or cements. Some embodiments may not include the flange members 140, 144 and the perimeter member 152 may be coupled merely to the exterior perimeter 154.

The perimeter member 152 is configured to contract under reduced pressure. It should be apparent that the perimeter member 152 does not contract in and of itself under the influence of reduced pressure but indirectly as the sealing member 112 presses upon the perimeter member 152. The sealing member 112 presses upon the perimeter member 152 as the sealed space 114 is evacuated by the application of reduced pressure. In some embodiments, the perimeter member 152 and distribution manifold 110 have the same initial height and substantially contract the same amount under reduced pressure. For example, the distribution manifold 110 may have an initial height 156 of $h_{d1}$ when not subjected to reduced pressure, and the fistula-isolating device 106 may have an initial height $h_{f1}$ when not subjected to reduced pressure. The heights are with respect to a component in a wound bed 102. Initially, $h_{d1}$ is substantially equal to $h_{f1}$. Similarly, the distribution manifold 110 may have a height $h_{d2}$ when subjected to reduced pressure at a first therapeutic pressure (for example, but not by way of limitation, −75 to −175 mm Hg), and the fistula-isolating device 106 may have a height $h_{f2}$ when subjected to reduced pressure at the first therapeutic pressure. The heights may be substantially the same, i.e., $h_{d2}$ is substantially equal to $h_{f2}$.

In some illustrative embodiments, the perimeter member 152 is made from the same material as the distribution manifold 110. For example, in one illustrative embodiment, both the distribution manifold 110 and the perimeter member 152 are made from an open cell foam, such as a GranuFoam® material from Kinetic Concepts, Incorporated of San Antonio, Tex. The perimeter member 152 may be made from other substances that allow fluid flow and that function to help the adjustable passageway member 148 adjust to or take on different heights. For example, the perimeter member 152 may be formed from one or more of the following: a fluid permeable material that functions as an isotropic spring, a resilient material (e.g. a foam or elastic member), or other material may be used. The perimeter member 152 and adjustable passageway 148 substantially rise and fall with the movement of the distribution manifold 110. In other words, the perimeter member 152 and adjustable passageway 148 substantially mimic the movement of the distribution manifold 110. The perimeter member 152, in one illustrative embodiment, may be relatively small pieces of foam or other manifold material and may be loosely placed around the adjustable passageway 148. Similarly, in one embodiment, the distribution manifold 110 may be an array of pieces of foam and the opening in which the fistula-isolating device 106 is disposed may be an opening or clearance in the array of pieces of foam. "Around," as used herein, means in the relative vicinity of an object and surrounding the object over at least 140 degrees and more typically over 180 degrees.

The adjustable passageway member 148 may be made from a thin flexible material that may be compressed or extended with the perimeter member 152. The flexible material may be, without limitation, a medical grade polymer or elastomers such as Silicone, polyurethane, TPE, TPU, PEBAX, TPO, nitrile, butyl and EVA. The adjustable passageway member 148 may comprise an annular wall member 158 having a thickness 0.25 mm to 3 mm or more. In one illustrative embodiment, the annular wall member 158 is less than 1 mm thick. The annular wall member 158 may contain bellows 160 (FIGS. 2 and 6) or collapsible folds 162 (FIGS. 7-9) that readily allow the fistula-isolating device 106 to expand and retract longitudinally along with the perimeter member 152. The second flange member 144 may include grooves 164 or visual indicia (by analogy see 190 in FIG. 7) to facilitate cutting the flange member 144 to a smaller size if a smaller flange member is desired near the fistula 104.

Figure 2:
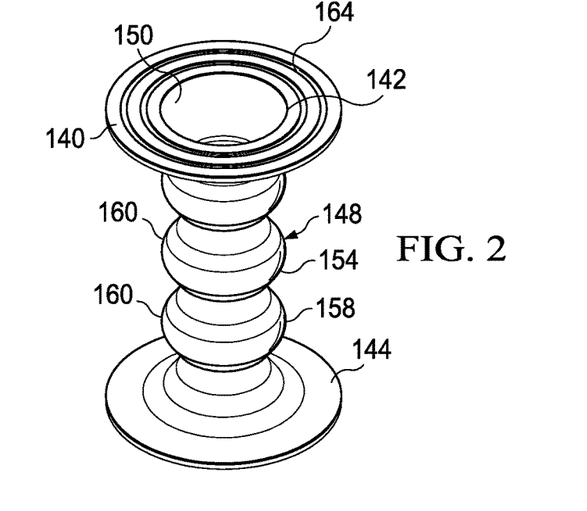
FIG. 2 is a schematic, perspective view of an illustrative embodiment of an adjustable passageway member and flange members of a fistula-isolating device.

The illustrative embodiment of the adjustable passageway 148 of FIG. 2 varies some from the illustrative embodiment of the adjustable passageway 148 included in FIGS. 3A and 3B mainly in the thickness of the adjustable passageway 148 and the size of the flange members 140, 144 that have been coupled. The embodiment of the adjustable passageway 148 of FIGS. 3A-3B may rely exclusively on pressure on the second flange member 144 that is delivered by the perimeter member 152 to provide a seal against the wound bed 102. In this embodiment, the adjustable passageway 148 may not carry a force structurally itself. In contrast, the embodiment of the adjustable passageway 148 of FIG. 2 may use an attachment device, e.g., ostomy paste, or other device, and may carry some of the structural forces such as providing a compressive force on the perimeter member 152. In other words, in some embodiments, the free length of the adjustable passageway 148 may be less than the length realized when the fistula-isolating device 106 is in the extended position. Accordingly, a tensile force is applied between the flanges 140, 144 and thereby delivers a compressive foce to the perimeter member 152.

Referring again to FIGS. 1-3B, the first flange member 140, second flange member 144, and adjustable passage way 148 provide a passageway 150 through which any effluent from the fistula 104 passes without interfering with the reduced pressure therapy administered by the distribution manifold 110 to the wound bed 102. To receive the effluent, the ostomy appliance 122 is fluidly coupled to the first flange aperture 142 of the passageway 150 by the ostomy-appliance interface 124. It should be apparent that the fluid coupling of the ostomy-appliance interface 124 to the first flange aperture 142 is through the ostomy-interface aperture 182 in the sealing member 112. The ostomy appliance 122 may be any form of device for receiving effluent from the fistula 104. For example, the ostomy appliance may be an off-the-shelf ostomy pouch, such as those available from Combitech, Coloplast, or Hollistser.

The ostomy-appliance interface 124 may be take numerous forms, such as a base plate 166 (FIG. 6) attached to the first flange member 140, or, as shown in FIG. 1, an attachment ring 168 with a first ostomy-attachment device 170 and a second ostomy-attachment device 174. In one illustrative embodiment, the ostomy-appliance interface 124 may be a stomahesive wafer. The ostomy-appliance interface 124 may also be a snap on collar or base plate, an adhesive skirt, or other device. In one illustrative embodiment, the ostomy-appliance interface 124 is a thin film, e.g., a drape-like material, and in others a thicker body.

Figure 4:
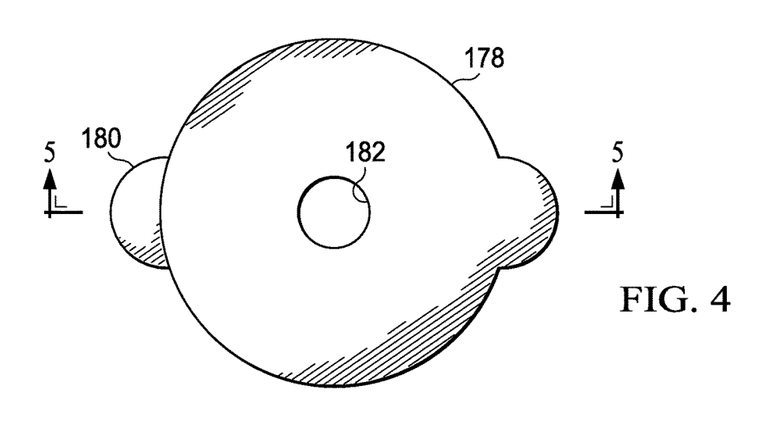
FIG. 4 is a schematic top view of an illustrative embodiment of an ostomy-appliance interface.
Figure 5:
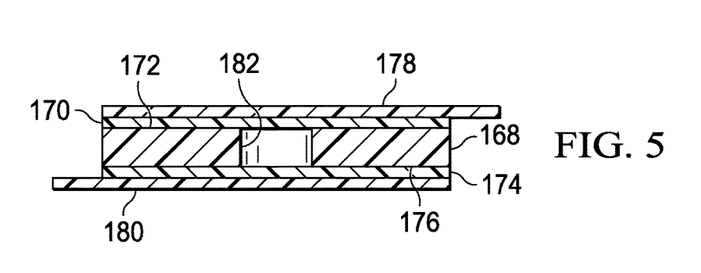
FIG. 5 is a schematic cross section of the ostomy-appliance interface of FIG. 4 taken along line 5-5.

Referring now primarily to FIGS. 1 and 4-5, an illustrative embodiment that uses the attachment ring 168 as the ostomy-appliance interface 124 will be presented. The first ostomy-attachment device 170 may be on a first side 172 of the attachment ring 168, and the second ostomy-attachment device 174 may be on the second, patient-facing side 176 of the attachment ring 168. The ostomy-attachment devices 170, 174 may be, for example, a pressure sensitive adhesive, cohesive seal (e.g., an Eakin's Ring), or a paste strip (e.g., Coloplast® Ostomy Paste Strip). In a before-use state, the first ostomy-attachment device 170 may be covered by a first release liner 178, and the second ostomy-attachment device 174 may be covered by a second release liner 180. The attachment ring 168 has an ostomy-interface aperture 182 that is positioned, at least in part, over the passageway 150.

Figure 6:
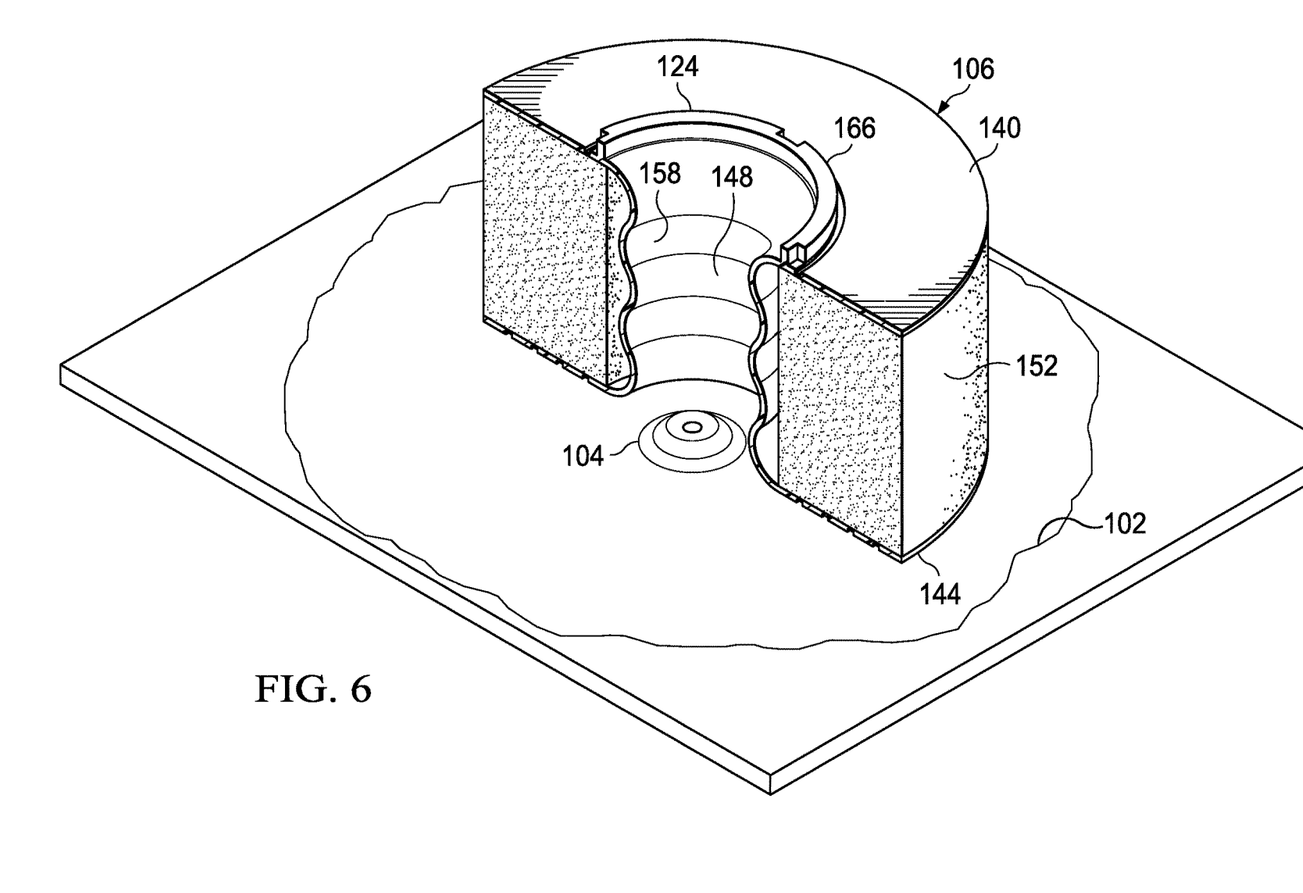
FIG. 6 is a schematic, partial perspective, partial cross section of an illustrative embodiment of a fistula-isolating device.

Referring now generally to FIG. 6, in another illustrative embodiment, the ostomy-appliance interface 124 may include the base plate 166 that may directly attach to a device on an ostomy appliance (not explicitly shown). Other aspects of the fistula-isolating device 106 of FIG. 6 are analogous to those previously presented.

Referring now to FIGS. 1-6, according to one illustrative embodiment, in operation, the healthcare provider sizes the distribution manifold 110 to be approximately the size of the wound bed 102. A fistula aperture 108 is formed in the distribution manifold 110 at the location that substantially aligns with the fistula 104. In some embodiments, the fistula aperture 108 may be preformed and then aligned with the fistula 104 before the distribution manifold 110 is cut to fit the wound bed 102. The distribution manifold 110 is placed into the wound bed 102 with the fistula aperture 108 over the fistula 104. The fistula-isolating device 106 may be placed inside of the fistula aperture 108 before or after development of the distribution manifold 110. In some embodiments, the second flange member 144 is positioned directly against a portion of the wound bed 102 and will ultimately form the fluid seal using force from the perimeter member 152. In other embodiments, a sealing device, such as a stoma paste, adhesive, hydrocolloid, hydrogel, silicone gel, or other substance may be used to form a seal with the second flange member 144 and the wound bed 102 around the fistula 104.

The sealing member 112 may be placed over a portion of the intact epidermis 126, distribution manifold 110, and fistula-isolating device 106 to form the sealed space 114 over the wound bed 102. The attachment device 134 may be used to help provide a fluid seal between the sealing member 112 and the epidermis 126. If not already formed, the aperture 136 may be formed on the sealing member 112 and the reduced-pressure interface 116 applied through the aperture 136 to provide fluid communication to the sealed space 114. If not already made, an ostomy-interface aperture 182 may be formed in the sealing member 112 over the passageway 150 of the fistula-isolating device 106. The ostomy-appliance interface 124 may be applied to the ostomy-interface aperture 182 and the ostomy appliance 122 attached to the ostomy-appliance interface 124.

With respect to the ostomy-appliance interface 124 shown in FIGS. 4-5, the ostomy-appliance interface 124 may be attached by removing the second release liner 180 to expose the second ostomy-attachment device 174 and placing the ostomy-appliance interface 124 onto the first side of the sealing member 112 proximate to the passageway 150. The first release liner 178 may be removed to expose the first ostomy-attachment device 170, and then the ostomy appliance 122 may be attached using the first ostomy-attachment device 170. The ostomy appliance 122 is applied with an aperture 123 of the ostomy appliance 122 over the ostomy-appliance interface 124.

The reduced-pressure source 120 may be coupled to the reduced-pressure interface 116 using the reduced-pressure delivery conduit 118. The reduced-pressure source 120 is activated and reduced pressure is delivered through the reduced-pressure delivery conduit 118 into the sealed space 114, which includes the distribution manifold 110. The distribution manifold 110 contracts under the influence of reduced pressure. It should be apparent that the distribution manifold 110 does not contract in and of itself under reduced pressure, but as the sealed space 114 is evacuated by the reduced pressure and the sealing member 112 applies a compressing force on the distribution manifold 110. In addition, under the influence of reduced pressure in the sealed space 114, the perimeter member 152 of the fistula-isolating device 106 also contracts for the same reasons. Through the influence of the contraction of the perimeter member 152 directly, which may be coupled to the flange members 140, 144, or through the action of the sealing member 112 moving with the contraction of the distribution manifold 110, the fistula-isolating device 106 compresses and may substantially match the compression of the distribution manifold 110.

It should be noted that the flexibility of the second flange member 144 and the perimeter member 152 allow various shaped wound beds 102 to be readily accommodated by the fistula-isolating device 106. Moreover, it should be noted that the vertical height adjustment of the fistula-isolating device 106 is automatic in that the fistula-isolating device 106 will respond with the distribution manifold 110. Thus, if the distribution manifold 110 has an initial height $H_{d1}$ when not subjected to reduced pressure and the fistula-isolating device 106 has an initial height $H_{f1}$, then $H_{d1}$ is substantially equal to $H_{f1}$, and under reduced pressure, the height of the distribution manifold is $H_{d2}$ and the height of the fistula-isolating device 106 is $H_{f2}$, then $H_{d2}$ is substantially equal to $H_{f2}$.

In some embodiments, e.g., those that include the adjustable passageway 148 of the type shown in FIG. 2, as the fistula-isolating device 106 compresses, the bellows 160 of the adjustable passageway member 148 compress, or if the collapsible folds (see FIG. 7) are used, the collapsible folds collapse in order for the fistula-isolating device 106 to assume the position under the influence of reduced pressure. With the system 100, reduced pressure reaches all of the wound bed 102 in the sealed space 114 except for the portion isolated by the fistula-isolating device 106. It should also be noted that the system 100 may be deployed relatively quickly and requires only minimal cutting and customization by the healthcare provider. The system 100 may protect the epidermis 126 and the wound bed 102, contain effluent from the fistula 104, and provide patient mobility and comfort.

Referring now primarily to FIGS. 1 and 7-11, a fistula-isolating device 106 for isolating a fistula 104 in a wound bed 102 undergoing reduced-pressure treatment as part of a system 100 includes a body 184. The body 184 of the fistula-isolating device 106 is substantially frustro-conical in shape and has a passageway 150 with a first end 186 and a second end 188. At least a portion of the body 184 defines the passageway 150 and is fluid impermeable.

Figure 7:
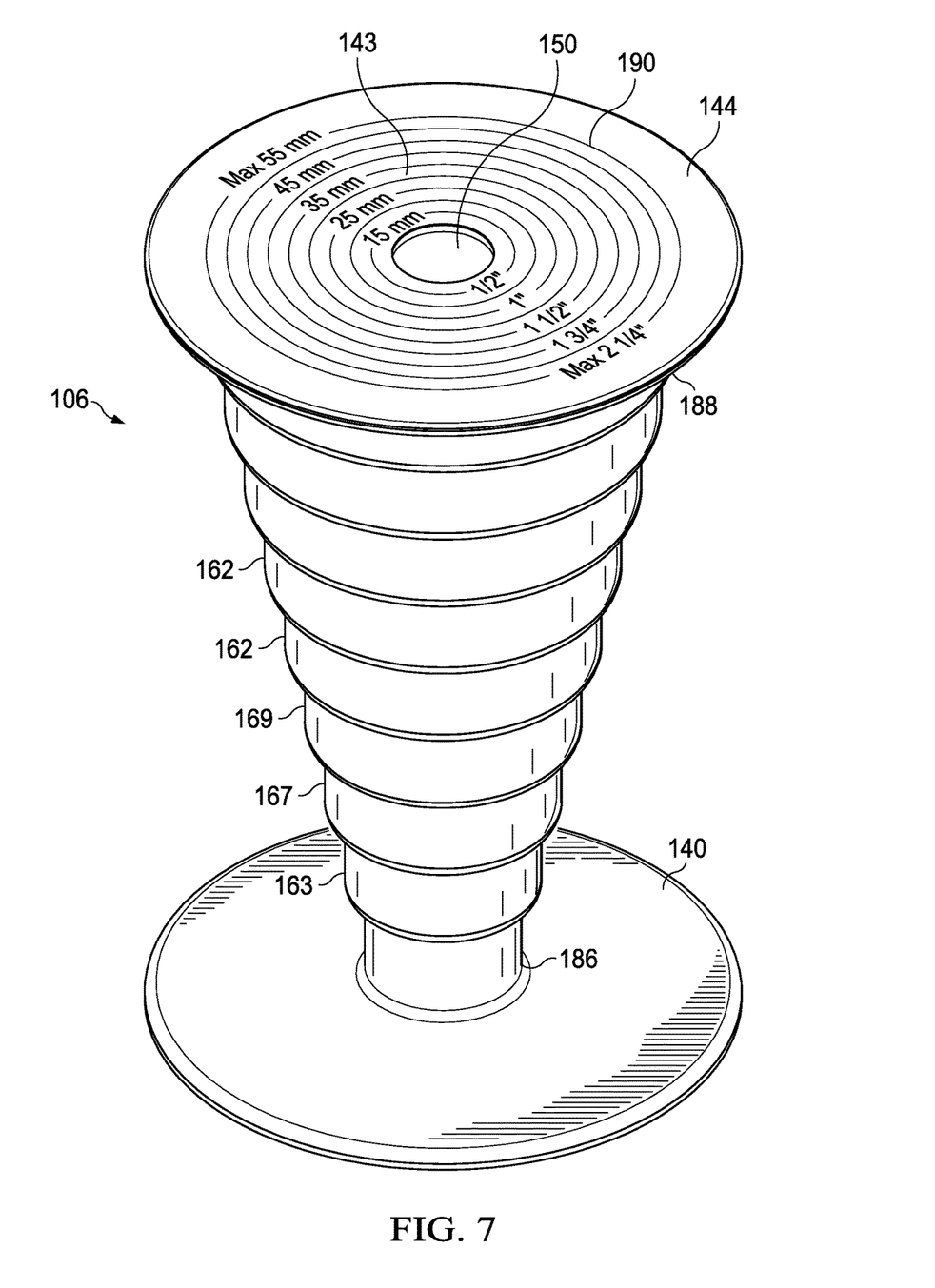
FIG. 7 is a schematic, perspective view of an illustrative embodiment of a fistula-isolating device.
Figure 8:
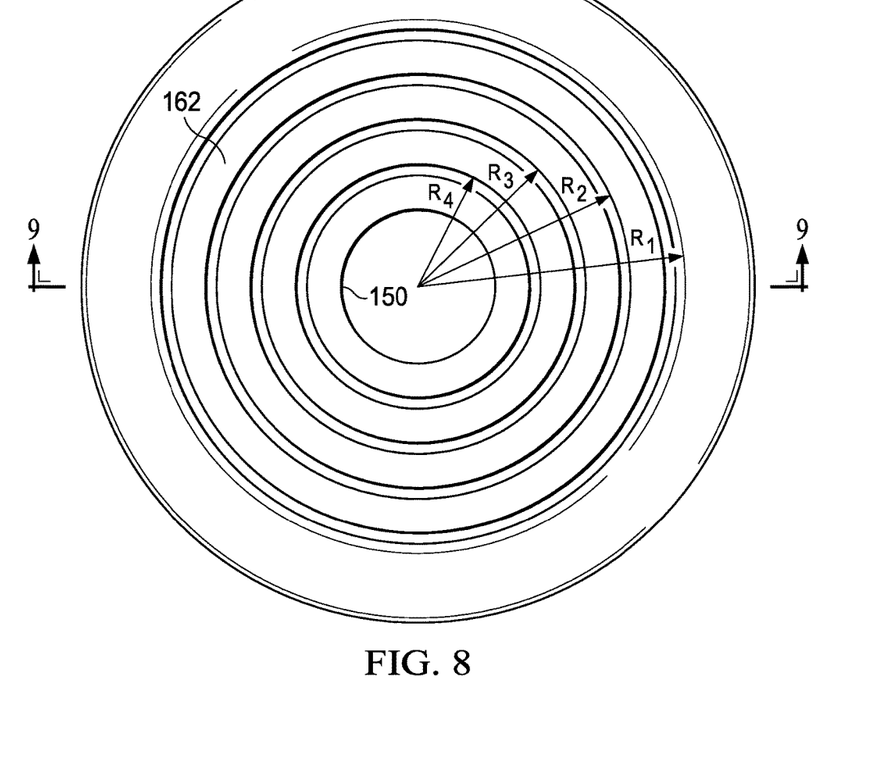
FIG. 8 is a schematic, plan view of the fistula-isolating device of FIG. 7 in a retracted state and with a portion of the first flange removed.
Figure 9:
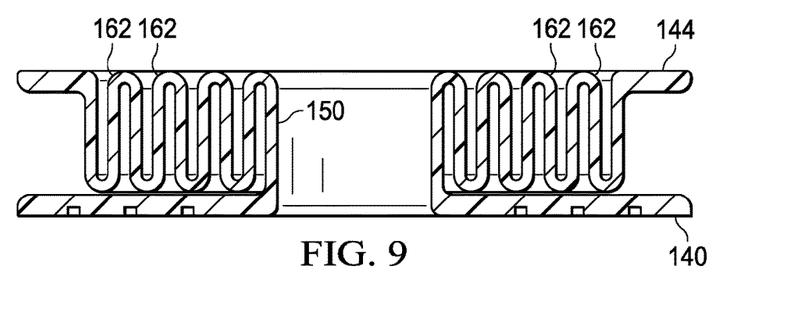
FIG. 9 is a schematic, cross-sectional view of the fistula-isolating device of FIGS. 7-8.

Referring now particularly to FIGS. 7-9, the fistula-isolating device 106 has the body 184 formed with collapsible folds 162 that allow the fistula-isolating device 106 to collapse to a one-fold high level as shown in FIG. 9 when in a retracted position. FIGS. 8 and 9 are shown without an optional extended portion 143 (FIG. 7) of the second flange 144. While the dimensions may vary in different embodiments, in one embodiment, the fully collapsed height of the fistula-isolating device 106 is approximately one centimeter and the extended position is approximately 10 centimeters. The collapsible folds 162 also allow the body 184 to go to an extended position as shown in FIG. 7. The body 184 may be formed with or have coupled a first flange member 140 and a second flange member 144. The second flange member 144, which is placed proximate to a portion of the wound bed 102, may be cut to the size of the fistula 104 opening, and visual indicia 190 may be included to show various possible cut patterns for different sizes as shown in FIG. 7. In other embodiments, e.g., FIGS. 10-11, no flange member may be included. The retracted position of the fistula-isolating device 106, among other things, may facilitate packaging and accommodate small depth wound beds.

The body 184 may have a first portion 163 having an external radius $R_1$, a second portion 167 having a second radius $R_2$, and a third portion 169 having a third radius $R_3$, wherein $R_1 > R_2 > R_3$. Similarly, additional portions with varying radii may be included as shown. This again is an arrangement that allows the collapsible folds 162 to fully collapse down to a single layer as shown in FIG. 9. In some embodiments, the first flange member 140 may be placed in the wound bed 102 and in another embodiment, the second flange member 144 may be placed in the wound bed 102.

Referring now primarily to FIGS. 1, and 7-9, according to one illustrative embodiment, in use, the distribution manifold 110 is sized and prepared for application against the wound bed 102 as previously presented. The fistula aperture 108 may be formed through the distribution manifold 110 to substantially accommodate the fistula-isolating device 106. In this embodiment, the second flange member 144 may include visual indicia 190, which may be used to help the healthcare provider to cut a portion of the second flange member 144 to accommodate the desired size around the fistula 104. Once the second flange member 144 has been sized as desired with respect to the beginning of the passageway 150, the second flange member 144 is placed against the wound bed 102 with the passageway 150 centered on the fistula 104.

The second flange member 144 may or may not be secured against the wound bed 102 using a device, such ostomy paste or those previously mentioned. The seal between the wound bed 102 and the second flange member 144 (or first flange member 140) may be formed in some embodiments only using the pressure that is asserted on the flange member 144 through the perimeter member 152. Pieces of distribution manifold 110 may be applied in the fistula aperture 108 between the flange members 140 and 144 to serve as a perimeter member, e.g., perimeter member 152 in FIG. 1. The remaining steps for applying the fistula-isolating device 106 are analogous to those previously presented with respect to FIGS. 1-6. It should be noted that with the design of the fistula-isolating device 106 of FIGS. 7-9, the fistula-isolating device 106 will contract or extend with the distribution manifold 110. Moreover, the fistula-isolating device 106 may take a variable position from a retracted position (FIG. 9) to an extended position (FIG. 7).

Figure 10:
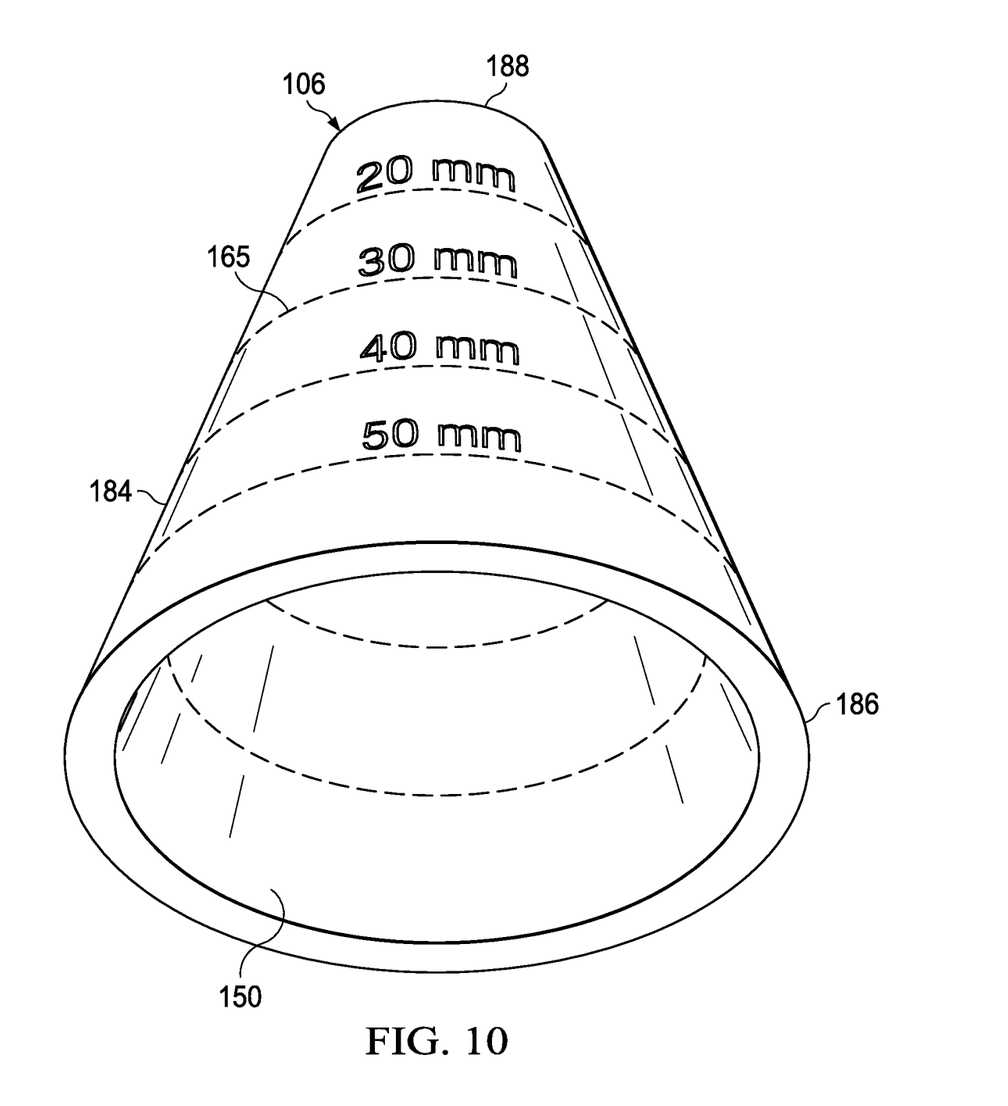
FIG. 10 is a schematic, perspective view of an illustrative embodiment of another fistula-isolating device.

Referring now primarily to FIG. 10, another illustrative embodiment of a fistula-isolating device 106 formed as a body 184 is presented. The fistula-isolating device has a frusto-conical shape or cone shape. The body 184 does not have flange members and is formed of a foam with a passageway 150 that is fluid impermeable. Visual indicia 165 may be printed on an exterior of the body 184 to facilitate cutting to size for various depths of wound beds 102. In some embodiments, the body 184 may be perforated to facilitate sizing by hand. The perforations may allow easy tearing of the body 184 to size the fistula-isolating device 106. The portion of the body 184 that renders the passageway 150 impermeable may not be perforated. The frusto-conical shape of the fistula-isolating device 106 may be made from a closed-cell foam or an open-cell foam with an impermeable layer on the passageway 150. The body 184 of this illustrative embodiment does not have bellows or collapsible folds and is not made generally to retract.

Referring now to FIGS. 1 and 10, the application of the system 100 using the fistula-isolating device 106 shown in FIG. 10 is analogous to those previously presented. In this particular embodiment, the body 184 may be cut using visual indicia 165 to accommodate a particular depth of the wound bed 102. Thus, for a more shallow wound, the cut may be made closer to a second end 188. After cutting as desired, the second end 188, and in particular the opening to the passageway 150, is placed around the fistula 104 through the fistula aperture 108 in the distribution manifold 110. The second end 188 may be sized with different opening sizes. For example, and not by way of limitation, in one embodiment, the opening is 0.25 inches (6.35 mm) and in another embodiment is 2 inches (50.8 mm). The opening may take other sizes as well. The length of the fistula-isolating device 106 may be any length desired and the healthcare provider may cut the fistula-isolating device 106 to the desired length. In one illustrative embodiment, the fistula-isolating device 106 has a longitudinal length of 4 to 5 inches (10.2 to 12.7 cm) but could be made longer or shorter.

The body 184 may be flexible enough to accommodate irregular shaped fistulas 104 and wound beds 102 and yet may be semi-rigid enough to prevent collapse under normal usage. Other aspects of applying the fistula-isolating device 106 of FIG. 10 are analogous to those previously discussed. It should be noted that the foam of the body 184 allows for accommodation of uneven wound beds 102 and other issues. The body 184 is highly customizable since the healthcare provider can easily cut the body 184 to size and can cut portions of the body 184 to better fit a wound bed 102. An inner surface of the passageway 150 is impermeable and so effluent from the fistula is carried through the passageway 150 and ultimately to the ostomy appliance 122.

Figure 11:
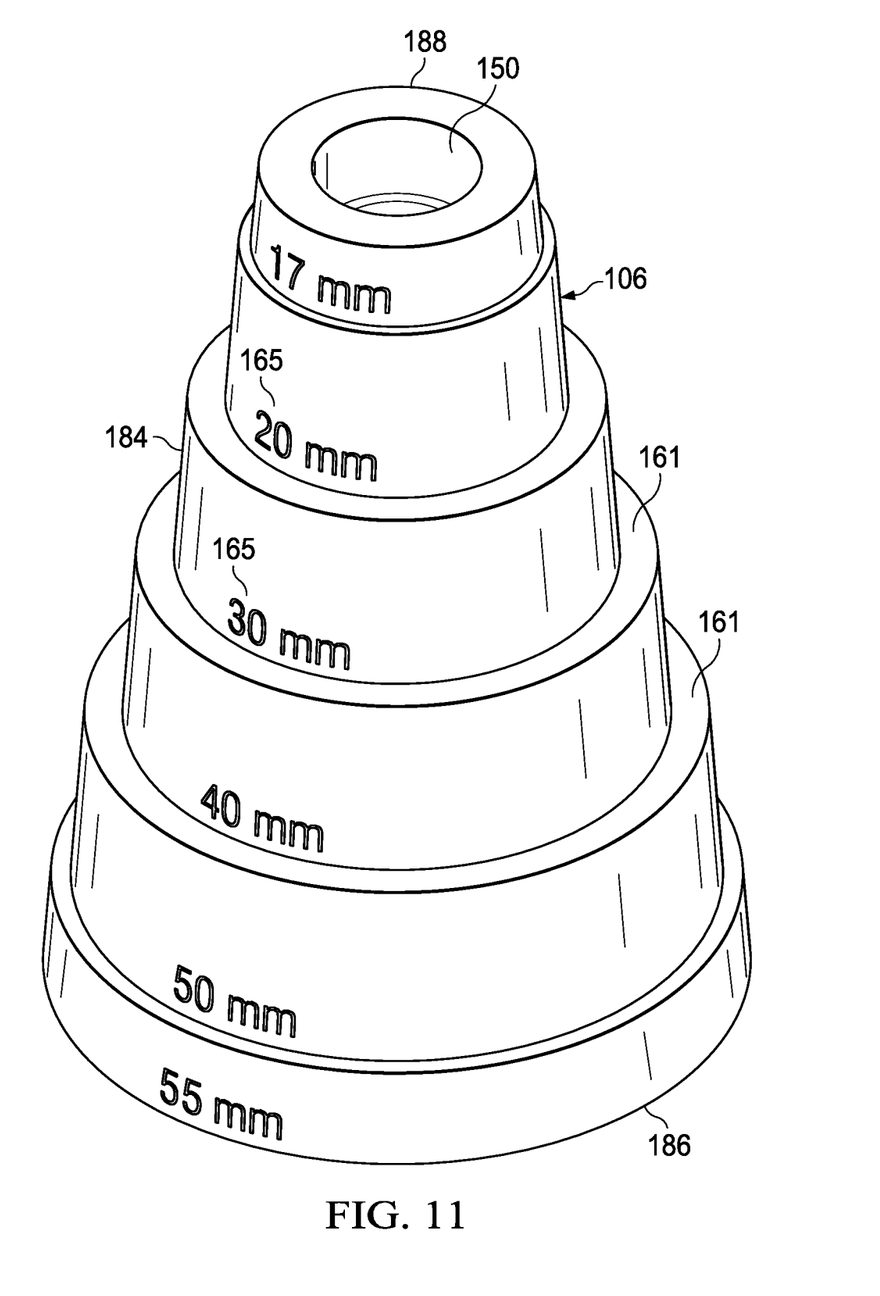
FIG. 11 is a schematic, perspective view of still another illustrative embodiment of a fistula-isolating device.

Referring now primarily to FIGS. 1 and 11, another illustrative embodiment of a fistula-isolating device 106 is presented. The fistula-isolating device 106 is made from a medical polymer and has steps 161 and no flange members. The fistula-isolating device 106 includes a passageway 150. Visual indicia 165 may be included for sizing. The fistula-isolating device 106 of FIG. 11 may be applied in a system 100 in a manner analogous to those previously presented. In this embodiment, however, the fistula-isolating device 106 is sized by cutting the body 184 along a step 161 or other visual indicia (analogous to 165 in FIG. 9). The visual indicia 165 may be included to help with sizing for the depth of the wound bed 102. Once sized, the second end 188 is typically placed around the fistula 104. It should be noted, that in this and other embodiments, the larger opening on the first end 186 may be applied around the fistula 104 in some situations. The fistula-isolating device 106 may be formed from a material that is flexible enough to accommodate irregular shaped fistulas 104 and wound beds 102 and yet semi-rigid enough to prevent collapse under normal usage.

In one illustrative embodiment, the fistula-isolating device 106 and the ostomy-appliance interface 124 may be contained within a single kit (not shown). The kit may have molded compartments to protect, for example, the flange members 140, 144 of the fistula-isolating device 106 for the embodiments of FIGS. 1-3B and 6-9. The kit accommodates storage and application by the healthcare provider.

According to one illustrative embodiment, the reduced-pressure source 120 may be micro-pump that is located at least partially in the sealed space 114. An inlet (not shown) may provide reduced pressure to the sealed space and a vent (not shown) may be used to exhaust positive pressure to an exterior of the sealing member 112. The reduced-pressure interface in such an embodiment is the inlet from the micro-pump.

Referring to FIGS. 2 and 3A, in another illustrative embodiment, the adjustable passageway member 148 may be formed with the ability to stretch and have the longitudinal dimension of the adjustable passageway member 148 modified, but has a relatively greater rigidity in a radial direction. The rigidity in the radial direction may help maintain the size of the passageway 150 even when the sealed space is subject to reduced pressure and pull outwards on the adjustable passageway member 148.

Although the present invention and its advantages have been disclosed in the context of certain illustrative, non-limiting embodiments, it should be understood that various changes, substitutions, permutations, and alterations can be made without departing from the scope of the invention as defined by the appended claims. It will be appreciated that any feature that is described in connection to any one embodiment may also be applicable to any other embodiment. The fistula-isolating devices 106 herein are analogous in many respects in each figure and accordingly, some parts are labeled in later figures but not further discussed.

It will be understood that the benefits and advantages described above may relate to one embodiment or may relate to several embodiments. It will further be understood that reference to "an" item refers to one or more of those items. As used herein, substantially means at least within ten percent.

The steps of the methods described herein may be carried out in any suitable order, or simultaneously where appropriate.

Where appropriate, aspects of any of the embodiments described above may be combined with aspects of any of the other embodiments described to form further examples having comparable or different properties and addressing the same or different problems.

As will be appreciated by the reader, each of the embodiments of fistula-isolating devices 106 described herein provide a passageway 148 through a region of reduced pressure 114 being utilized to treat a wound bed 102 such that effluent can be removed from that fistula 104 without entering the region of reduced pressure 114. The fistula-isolating devices 106 therefore provide a means for isolating part of a region under a sealing member 112 to allow extraction of effluent from a fistula 104. To accommodate changes in the distance between the wound bed 102 and the sealing member 112 the fistula-isolating device 106 may have a variable length, and may be provided with a resilient member 152 acting to extend the fistula-isolating device 106. Alternatively, the fistula-isolating device 106 may be formed of a resilient material.

It will be understood that the above description of preferred embodiments is given by way of example only and that various modifications may be made by those skilled in the art. The above specification, examples and data provide a complete description of the structure and use of exemplary embodiments of the invention. Although various embodiments of the invention have been described above with a certain degree of particularity, or with reference to one or more individual embodiments, those skilled in the art could make numerous alterations to the disclosed embodiments without departing from the scope of the claims.

We claim:

1. A system for providing reduced pressure treatment to a wound bed that includes a fistula, the system comprising:
   a fistula-isolating device for isolating the fistula in the wound bed undergoing reduced-pressure treatment, the fistula-isolating device comprising:
      a body that is substantially frusto-conical in shape and having a passageway and having a first end and a second end, and
      a perimeter member positioned substantially around an exterior of the body and substantially along a length of the body,
      wherein at least a portion of the body defining the passageway is fluid impermeable;
   a distribution manifold having a fistula aperture for receiving the fistula-isolating device;
   a sealing member for covering the fistula-isolating device and the distribution manifold to create a sealed space over at least a portion of the wound bed, wherein the sealing member has an ostomy-interface aperture;
   a reduced-pressure source for supplying a reduced pressure to the sealed space; and
   an ostomy appliance fluidly coupled to the fistula-isolating device.

2. The system of claim 1 wherein the fistula-isolating device further comprises visual indicia on an exterior of the frusto-conical body showing where sizing cuts may be made.

3. The system of claim 1, wherein the body has a first portion having an external radius $R_1$, a second portion having a second radius $R_2$, and a third portion having a third radius $R_3$, wherein $R_1 > R_2 > R_3$.

4. The system of claim 1, wherein the distribution manifold has an initial height $h_{d1}$ when not subjected to reduced pressure, wherein the fistula-isolating device has an initial height $h_{F1}$ when not subjected to reduced pressure, and wherein $h_{d1}$ is substantially equal to $h_{F1}$.

5. The system of claim 1, wherein
   the distribution manifold has an initial height $h_{d1}$ when not subjected to reduced pressure;
   the fistula-isolating device has an initial height $h_{F1}$ when not subjected to reduced pressure and $h_{d1}$ is substantially equal to $h_{F1}$;
   the distribution manifold has a height $h_{d2}$ when the sealed space is subjected to reduced pressure in a first therapeutic pressure range; and
   the fistula-isolating device has a height $h_{F2}$ when the sealed space is subjected to reduced pressure at the first therapeutic pressure, wherein $h_{d2}$ is substantially equal to $h_{F2}$.

6. The system of claim 1, wherein the body of the fistula-isolating device comprises a first material and the distribution manifold comprises the first material.

7. The system of claim 1, wherein the body of the fistula-isolating device comprises a closed-cell foam.

8. The system of claim 1, wherein the body of the fistula-isolating device comprises an open-cell foam and an impermeable layer along the passageway.

9. A fistula-isolating device for isolating a fistula in a wound bed undergoing reduced-pressure treatment, the fistula-isolating device comprising:
   a body that is substantially frusto-conical in shape and having a plurality of segments and a passageway;
   wherein at least a portion of the body defining the passageway is fluid impermeable; and
   wherein at least one of the plurality of segments is adapted to be removed for adjusting a height of the body of the fistula-isolating device.

10. The fistula-isolating device of claim 9, wherein the body comprises a foam.

11. The fistula-isolating device of claim 10, wherein the foam is an open-cell foam.

12. The fistula-isolating device of claim 9, wherein the device has a length of 4 to 5 inches.

13. The fistula-isolating device of claim 9, further comprising visual indicia on an exterior of the frusto-conical body showing where sizing cuts may be made.

14. The fistula-isolating device of claim 9, wherein the body has a first segment having an external radius $R_1$, a second segment having a second radius $R_2$, and a third segment having a third radius $R_3$, wherein $R_1 > R_2 > R_3$.

* * * * *